(12) United States Patent
Francischelli et al.

(10) Patent No.: US 8,333,764 B2
(45) Date of Patent: Dec. 18, 2012

(54) DEVICE AND METHOD FOR DETERMINING TISSUE THICKNESS AND CREATING CARDIAC ABLATION LESIONS

(75) Inventors: David E. Francischelli, Anoka, MN (US); Eduardo N. Warman, Maple Grove, MN (US); Rahul Mehra, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 1341 days.

(21) Appl. No.: 10/844,213

(22) Filed: May 12, 2004

(65) Prior Publication Data
US 2005/0256522 A1 Nov. 17, 2005

(51) Int. Cl.
*A61B 18/14* (2006.01)
(52) U.S. Cl. .......................................... 606/51; 606/52
(58) Field of Classification Search .................... 606/34, 606/35, 50–52
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |

(Continued)

FOREIGN PATENT DOCUMENTS
WO 03-020139 3/2003
(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner* — Michael Peffley

(57) ABSTRACT

A tissue ablation device has a handle and an ablation head coupled to the handle. The ablation head has a first jaw, a second jaw, and an ablative element coupled to at least one of the first and second jaws. A thickness measurement device may be coupled to the ablation device to indicate the distance separating the first and second jaws. Further, a force measurement device may be coupled to the ablation device to measure the force being applied by the first and second jaws to a piece of tissue. Further, a strain measurement device may be coupled to the ablation device to indicate the strain resulting in a piece of tissue disposed between the first and second jaws when a stress is applied to the tissue.

3 Claims, 6 Drawing Sheets

U.S. PATENT DOCUMENTS

| | | | |
|---|---|---|---|
| 4,377,168 A | 3/1983 | Rzasa et al. | |
| 4,519,389 A | 5/1985 | Gudkin et al. | |
| 4,598,698 A | 7/1986 | Siegmund | |
| 4,601,290 A | 7/1986 | Effron et al. | |
| 4,664,110 A | 5/1987 | Schanzlin | |
| 4,736,749 A | 4/1988 | Lundback | |
| 4,779,611 A | 10/1988 | Grooters et al. | |
| 4,802,475 A | 2/1989 | Weshahy | |
| 4,815,470 A | 3/1989 | Curtis et al. | |
| 4,872,346 A | 10/1989 | Kelly-Fry et al. | |
| 4,916,922 A | 4/1990 | Mullens | |
| 4,917,095 A | 4/1990 | Fry et al. | |
| 4,936,281 A | 6/1990 | Stasz | |
| 4,946,460 A | 8/1990 | Merry et al. | |
| 5,013,312 A | 5/1991 | Parins et al. | |
| 5,029,574 A | 7/1991 | Shimamura et al. | |
| 5,044,165 A | 9/1991 | Linner et al. | |
| 5,078,713 A | 1/1992 | Varney | |
| 5,080,102 A | 1/1992 | Dory | |
| 5,080,660 A | 1/1992 | Buelna | |
| 5,100,388 A | 3/1992 | Behl et al. | |
| 5,108,390 A | 4/1992 | Potocky et al. | |
| 5,147,355 A | 9/1992 | Friedman et al. | |
| 5,178,133 A | 1/1993 | Pena | |
| 5,207,674 A | 5/1993 | Hamilton | |
| 5,217,860 A | 6/1993 | Fahy et al. | |
| 5,222,501 A | 6/1993 | Ideker et al. | |
| 5,224,943 A | 7/1993 | Goddard | |
| 5,228,923 A | 7/1993 | Hed | |
| 5,231,995 A | 8/1993 | Desai | |
| 5,232,516 A | 8/1993 | Hed | |
| 5,254,116 A | 10/1993 | Baust et al. | |
| 5,263,493 A | 11/1993 | Avitall | |
| 5,269,291 A | 12/1993 | Carter | |
| 5,275,595 A | 1/1994 | Dobak, III | |
| 5,277,201 A | 1/1994 | Stern | |
| 5,281,213 A | 1/1994 | Milder et al. | |
| 5,281,215 A | 1/1994 | Milder | |
| 5,295,484 A | 3/1994 | Marcus et al. | |
| 5,300,068 A | 4/1994 | Rosar et al. | 606/34 |
| 5,309,896 A | 5/1994 | Moll et al. | |
| 5,316,000 A | 5/1994 | Chapelon et al. | |
| 5,317,878 A | 6/1994 | Bradshaw et al. | |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowler | |
| 5,334,181 A | 8/1994 | Rubinsky et al. | |
| 5,334,193 A | 8/1994 | Nardella | 606/41 |
| 5,342,357 A | 8/1994 | Nardella | 606/40 |
| 5,348,554 A | 9/1994 | Imran et al. | |
| 5,353,783 A | 10/1994 | Nakao et al. | |
| 5,354,258 A | 10/1994 | Dory | |
| 5,361,752 A | 11/1994 | Moll et al. | |
| 5,385,148 A | 1/1995 | Lesh et al. | |
| 5,395,033 A * | 3/1995 | Byrne et al. | 227/175.1 |
| 5,396,887 A | 3/1995 | Imran | |
| 5,397,304 A | 3/1995 | Truckai | |
| 5,400,770 A | 3/1995 | Nakao et al. | |
| 5,400,783 A | 3/1995 | Pomeranz et al. | |
| 5,403,309 A | 4/1995 | Coleman et al. | |
| 5,403,311 A | 4/1995 | Abele et al. | 606/49 |
| 5,405,376 A | 4/1995 | Mulier et al. | |
| 5,409,483 A | 4/1995 | Campbell et al. | |
| 5,423,807 A | 6/1995 | Milder | |
| 5,423,811 A | 6/1995 | Imran et al. | |
| 5,427,119 A | 6/1995 | Swartz et al. | |
| 5,431,645 A | 7/1995 | Smith et al. | |
| 5,431,649 A | 7/1995 | Mulier et al. | 606/41 |
| 5,433,708 A | 7/1995 | Nichols et al. | 604/113 |
| 5,435,308 A | 7/1995 | Gallup et al. | |
| 5,437,651 A | 8/1995 | Todd et al. | |
| 5,437,664 A | 8/1995 | Cohen et al. | 606/42 |
| 5,443,463 A | 8/1995 | Stern et al. | |
| 5,443,470 A | 8/1995 | Stern et al. | |
| 5,450,843 A | 9/1995 | Moll et al. | |
| 5,452,582 A | 9/1995 | Longsworth | |
| 5,452,733 A | 9/1995 | Sterman et al. | |
| 5,456,682 A | 10/1995 | Edwards et al. | 606/31 |
| 5,462,545 A | 10/1995 | Wang et al. | |
| 5,465,717 A | 11/1995 | Imran et al. | |
| 5,469,853 A * | 11/1995 | Law et al. | 600/463 |
| 5,472,876 A | 12/1995 | Fahy | |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,496,312 A | 3/1996 | Klicek | |
| 5,497,774 A | 3/1996 | Swartz et al. | |
| 5,498,248 A | 3/1996 | Milder | |
| 5,500,012 A | 3/1996 | Brucker et al. | |
| 5,505,730 A | 4/1996 | Edwards | |
| 5,516,505 A | 5/1996 | McDow | |
| 5,520,682 A | 5/1996 | Baust et al. | |
| 5,522,870 A | 6/1996 | Ben-Zion | |
| 5,536,267 A | 7/1996 | Edwards et al. | |
| 5,542,928 A | 8/1996 | Evans et al. | 604/113 |
| 5,545,195 A | 8/1996 | Lennox et al. | |
| 5,545,200 A | 8/1996 | West et al. | |
| 5,549,661 A | 8/1996 | Kordis et al. | |
| 5,555,883 A | 9/1996 | Avitall | |
| 5,558,671 A | 9/1996 | Yates | |
| 5,560,362 A | 10/1996 | Sliwa, Jr. et al. | |
| 5,562,720 A | 10/1996 | Stern et al. | |
| 5,569,241 A | 10/1996 | Edwards | |
| 5,571,088 A | 11/1996 | Lennox et al. | |
| 5,571,215 A | 11/1996 | Sterman et al. | |
| 5,573,532 A | 11/1996 | Chang et al. | |
| 5,575,766 A | 11/1996 | Swartz et al. | |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,584,872 A | 12/1996 | LaFontaine et al. | 607/116 |
| 5,588,432 A | 12/1996 | Crowley | |
| 5,590,657 A | 1/1997 | Cain et al. | |
| 5,595,183 A | 1/1997 | Swanson et al. | |
| 5,607,462 A | 3/1997 | Imran | |
| 5,609,151 A | 3/1997 | Mulier et al. | 128/642 |
| 5,617,854 A | 4/1997 | Munsif | |
| 5,630,837 A | 5/1997 | Crowley | |
| 5,637,090 A | 6/1997 | McGee et al. | |
| 5,643,197 A | 7/1997 | Brucker et al. | |
| 5,653,692 A | 8/1997 | Masterson et al. | 604/113 |
| 5,656,029 A | 8/1997 | Imran et al. | |
| 5,658,278 A | 8/1997 | Imran et al. | |
| 5,671,747 A | 9/1997 | Connor | |
| 5,673,695 A | 10/1997 | McGee et al. | |
| 5,673,704 A | 10/1997 | Marchlinski et al. | 128/739 |
| 5,676,662 A | 10/1997 | Fleischhacker et al. | |
| 5,676,692 A | 10/1997 | Sanghvi et al. | |
| 5,676,693 A | 10/1997 | LaFontaine | 607/116 |
| 5,678,550 A | 10/1997 | Bassen et al. | |
| 5,680,860 A | 10/1997 | Imran | |
| 5,681,278 A | 10/1997 | Igo et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | |
| 5,697,909 A | 12/1997 | Eggers et al. | 604/114 |
| 5,697,925 A | 12/1997 | Taylor | |
| 5,697,927 A | 12/1997 | Imran et al. | 606/41 |
| 5,697,928 A | 12/1997 | Walcott et al. | |
| 5,713,942 A | 2/1998 | Stern et al. | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,720,775 A | 2/1998 | Larnard | |
| 5,722,402 A | 3/1998 | Swanson et al. | |
| 5,725,524 A | 3/1998 | Mulier et al. | 606/41 |

| | | | |
|---|---|---|---|
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | |
| 5,733,281 A | 3/1998 | Nardella | 606/38 |
| 5,735,280 A | 4/1998 | Sherman et al. | |
| 5,735,290 A | 4/1998 | Sterman et al. | |
| 5,749,869 A | 5/1998 | Lindenmeier et al. | 606/34 |
| 5,755,760 A | 5/1998 | Maguire et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,960 A | 8/1998 | Stevens et al. | |
| 5,800,428 A | 9/1998 | Nelson et al. | |
| 5,800,482 A | 9/1998 | Pomeranz et al. | 607/101 |
| 5,807,395 A | 9/1998 | Mulier et al. | 606/41 |
| 5,810,802 A | 9/1998 | Panescu et al. | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,860,951 A * | 1/1999 | Eggers et al. | 604/510 |
| 5,868,739 A | 2/1999 | Lindènmeier et al. | 606/39 |
| 5,871,523 A | 2/1999 | Fleischman et al. | |
| 5,871,525 A | 2/1999 | Edwards et al. | |
| 5,873,845 A | 2/1999 | Cline et al. | |
| 5,876,357 A * | 3/1999 | Tomer | 600/591 |
| 5,876,398 A | 3/1999 | Mulier et al. | 606/41 |
| 5,876,399 A | 3/1999 | Chia et al. | |
| 5,879,295 A | 3/1999 | Li et al. | |
| 5,879,296 A | 3/1999 | Ockuly et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,888,198 A | 3/1999 | Eggers et al. | 604/114 |
| 5,891,095 A | 4/1999 | Eggers et al. | 604/114 |
| 5,893,848 A | 4/1999 | Negus et al. | |
| 5,895,417 A | 4/1999 | Pomeranz et al. | 607/101 |
| 5,897,553 A | 4/1999 | Mulier et al. | 606/41 |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,902,328 A | 5/1999 | LaFontaine et al. | 607/116 |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,906,613 A | 5/1999 | Mulier et al. | 606/41 |
| 5,908,029 A | 6/1999 | Knudson et al. | |
| 5,913,854 A | 6/1999 | Maguire et al. | 606/41 |
| 5,916,213 A | 6/1999 | Haissaguerre et al. | |
| 5,916,214 A | 6/1999 | Cosio et al. | |
| 5,921,924 A | 7/1999 | Avitall | |
| 5,921,982 A | 7/1999 | Lesh et al. | |
| 5,927,284 A | 7/1999 | Borst et al. | |
| 5,928,191 A | 7/1999 | Houser et al. | |
| 5,931,810 A | 8/1999 | Grabek | |
| 5,931,848 A | 8/1999 | Saadat | |
| 5,954,661 A | 9/1999 | Greenspon et al. | |
| 5,971,980 A | 10/1999 | Sherman | |
| 5,971,983 A | 10/1999 | Lesh | |
| 5,976,128 A | 11/1999 | Schilling et al. | 606/34 |
| 5,993,447 A | 11/1999 | Blewett et al. | |
| 6,007,499 A | 12/1999 | Martin et al. | |
| 6,012,457 A | 1/2000 | Lesh | |
| 6,016,811 A | 1/2000 | Knopp et al. | |
| 6,042,556 A | 3/2000 | Beach et al. | |
| 6,063,081 A | 5/2000 | Mulier | |
| 6,071,279 A | 6/2000 | Whayne et al. | |
| 6,083,223 A * | 7/2000 | Baker | 606/52 |
| 6,088,894 A | 7/2000 | Oakley | |
| 6,096,037 A * | 8/2000 | Mulier et al. | 606/49 |
| 6,113,592 A | 9/2000 | Taylor | |
| 6,117,101 A | 9/2000 | Diederich et al. | |
| 6,120,496 A | 9/2000 | Whayne et al. | |
| 6,142,993 A | 11/2000 | Whayne et al. | |
| 6,142,994 A | 11/2000 | Swanson et al. | |
| 6,152,920 A | 11/2000 | Thompson et al. | |
| 6,161,543 A | 12/2000 | Cox et al. | |
| 6,165,174 A | 12/2000 | Jacobs et al. | |
| 6,216,704 B1 * | 4/2001 | Ingle et al. | 128/898 |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,235,027 B1 * | 5/2001 | Herzon | 606/51 |
| 6,237,605 B1 | 5/2001 | Vaska et al. | |
| 6,238,347 B1 | 5/2001 | Nix et al. | |
| 6,238,393 B1 | 5/2001 | Mulier | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |
| 6,251,128 B1 | 6/2001 | Knopp et al. | |
| 6,270,471 B1 | 8/2001 | Hechel et al. | |
| 6,293,943 B1 | 9/2001 | Panescu et al. | |
| 6,296,619 B1 | 10/2001 | Brisken et al. | |
| 6,302,880 B1 | 10/2001 | Schaer | |
| 6,311,692 B1 | 11/2001 | Vaska et al. | |
| 6,312,383 B1 | 11/2001 | Lizzi et al. | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,328,736 B1 | 12/2001 | Mulier | |
| 6,332,881 B1 | 12/2001 | Carner et al. | |
| 6,358,248 B1 | 3/2002 | Mulier | |
| 6,361,531 B1 | 3/2002 | Hissong | |
| 6,364,876 B1 | 4/2002 | Erb et al. | |
| 6,368,275 B1 | 4/2002 | Sliwa et al. | |
| 6,371,955 B1 | 4/2002 | Fuimaono et al. | |
| 6,383,151 B1 | 5/2002 | Diederich et al. | |
| 6,385,472 B1 | 5/2002 | Hall et al. | |
| 6,398,792 B1 | 6/2002 | O'Connor | |
| 6,409,722 B1 | 6/2002 | Hoey | |
| 6,413,254 B1 | 7/2002 | Hissong et al. | |
| 6,419,648 B1 | 7/2002 | Vitek et al. | |
| 6,425,867 B1 | 7/2002 | Vaezy et al. | |
| 6,430,426 B2 | 8/2002 | Avitall | |
| 6,440,130 B1 | 8/2002 | Mulier | |
| 6,443,952 B1 | 9/2002 | Mulier | |
| 6,447,507 B1 | 9/2002 | Bednarek et al. | |
| 6,461,314 B1 | 10/2002 | Pant et al. | |
| 6,461,356 B1 | 10/2002 | Patterson | |
| 6,464,700 B1 | 10/2002 | Koblish et al. | |
| 6,471,697 B1 | 10/2002 | Lesh | |
| 6,471,698 B1 | 10/2002 | Edwards et al. | |
| 6,474,340 B1 | 11/2002 | Vaska et al. | |
| 6,475,216 B2 | 11/2002 | Mulier | |
| 6,477,396 B1 | 11/2002 | Mest et al. | |
| 6,484,727 B1 | 11/2002 | Vaska et al. | |
| 6,488,680 B1 * | 12/2002 | Francischelli et al. | 606/41 |
| 6,502,575 B1 | 1/2003 | Jacobs et al. | |
| 6,514,250 B1 | 2/2003 | Jahns | |
| 6,527,767 B2 | 3/2003 | Wang et al. | |
| 6,537,248 B2 | 3/2003 | Mulier | |
| 6,537,272 B2 | 3/2003 | Christopherson et al. | |
| 6,558,382 B2 | 5/2003 | Jahns | |
| 6,562,037 B2 * | 5/2003 | Paton et al. | 606/51 |
| 6,582,451 B1 * | 6/2003 | Marucci et al. | 606/207 |
| 6,584,360 B2 * | 6/2003 | Francischelli et al. | 607/98 |
| 6,585,732 B2 | 7/2003 | Mulier | |
| 6,605,084 B2 | 8/2003 | Acker et al. | |
| 6,610,055 B1 | 8/2003 | Swanson et al. | |
| 6,610,060 B2 | 8/2003 | Mulier | |
| 6,613,048 B2 | 9/2003 | Mulier | |
| 6,645,199 B1 | 11/2003 | Jenkins et al. | |
| 6,648,883 B2 * | 11/2003 | Francischelli et al. | 606/41 |
| 6,656,175 B2 | 12/2003 | Francischelli | |
| 6,660,001 B2 * | 12/2003 | Gregory | 606/15 |
| 6,663,627 B2 | 12/2003 | Francischelli | |
| 6,692,450 B1 | 2/2004 | Coleman | |

| | | | |
|---|---|---|---|
| 6,699,240 B2 | 3/2004 | Francischelli | |
| 6,702,811 B2 | 3/2004 | Stewart et al. | |
| 6,706,038 B2 | 3/2004 | Francischelli et al. | |
| 6,706,039 B2 | 3/2004 | Mulier | |
| 6,716,211 B2 | 4/2004 | Mulier | |
| 6,736,810 B2 | 5/2004 | Hoey | |
| 6,755,827 B2 | 6/2004 | Mulier | |
| 6,764,487 B2 | 7/2004 | Mulier | |
| 6,773,433 B2 | 8/2004 | Stewart et al. | |
| 6,776,780 B2 | 8/2004 | Mulier | |
| 6,807,968 B2 | 10/2004 | Francischelli | |
| 6,827,715 B2 | 12/2004 | Francischelli | |
| 6,849,073 B2 | 2/2005 | Hoey | |
| 6,858,028 B2 | 2/2005 | Mulier | |
| 6,887,238 B2 | 5/2005 | Jahns | |
| 6,899,711 B2 | 5/2005 | Stewart et al. | |
| 6,911,019 B2 | 6/2005 | Mulier | |
| 6,916,318 B2 | 7/2005 | Francischelli | |
| 6,936,046 B2 | 8/2005 | Hissong | |
| 6,949,097 B2 | 9/2005 | Stewart et al. | |
| 6,949,098 B2 | 9/2005 | Mulier | |
| 6,960,205 B2 | 11/2005 | Jahns | |
| 6,962,589 B2 | 11/2005 | Mulier | |
| 7,025,764 B2 * | 4/2006 | Paton et al. | 606/34 |
| 7,267,677 B2 * | 9/2007 | Johnson et al. | 606/51 |
| 2001/0039417 A1 * | 11/2001 | Harano et al. | 606/40 |
| 2002/0052599 A1 * | 5/2002 | Goble | 606/40 |
| 2002/0091384 A1 | 7/2002 | Hooven et al. | |
| 2002/0091385 A1 * | 7/2002 | Paton et al. | 606/51 |
| 2002/0120267 A1 * | 8/2002 | Phan | 606/51 |
| 2003/0018329 A1 * | 1/2003 | Hooven | 606/41 |
| 2003/0045872 A1 | 3/2003 | Jacobs | |
| 2003/0144656 A1 | 7/2003 | Ocel | |
| 2003/0171745 A1 * | 9/2003 | Francischelli et al. | 606/41 |
| 2003/0191462 A1 | 10/2003 | Jacobs | |
| 2003/0195384 A1 * | 10/2003 | Francischelli et al. | 600/34 |
| 2003/0199869 A1 * | 10/2003 | Johnson et al. | 606/50 |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0044340 A1 | 3/2004 | Francischelli | |
| 2004/0049179 A1 | 3/2004 | Francischelli | |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0143263 A1 * | 7/2004 | Schechter et al. | 606/51 |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0267252 A1 * | 12/2004 | Washington et al. | 606/27 |
| 2004/0267326 A1 | 12/2004 | Ocel | |
| 2005/0010095 A1 | 1/2005 | Stewart et al. | |
| 2005/0033278 A1 * | 2/2005 | McClurken et al. | 606/41 |
| 2005/0033280 A1 | 2/2005 | Francischelli | |
| 2005/0090815 A1 | 4/2005 | Francischelli | |
| 2005/0113828 A1 * | 5/2005 | Shields et al. | 606/51 |
| 2005/0143729 A1 | 6/2005 | Francischelli | |
| 2005/0165392 A1 | 7/2005 | Francischelli | |
| 2005/0209564 A1 | 9/2005 | Bonner | |
| 2005/0256522 A1 | 11/2005 | Francischelli et al. | |
| 2005/0267454 A1 | 12/2005 | Hissong | |
| 2006/0009756 A1 | 1/2006 | Francischelli | |
| 2006/0009759 A1 | 1/2006 | Chrisitian | |

FOREIGN PATENT DOCUMENTS

| WO | 03-090630 | 11/2003 |
|---|---|---|

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery , vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," *J of Thorac Cardiovasc Surg*, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

DEVICE AND METHOD FOR DETERMINING TISSUE THICKNESS AND CREATING CARDIAC ABLATION LESIONS

FIELD OF THE INVENTION

The present invention relates to tissue ablation devices generally, and more particularly to devices adapted to ablate lines of tissue, for example for use in conjunction with an electrosurgical version of the Maze procedure. More particularly, the invention relates to an ablation device that aids in the measurement of tissue thickness and monitoring the transmurality of lesions.

BACKGROUND OF THE INVENTION

Various types of electrophysiology devices are used for ablating tissue. Typically, such devices include a conductive tip or blade which serves as one electrode in an electrical circuit which is completed via a grounding electrode coupled to the patient. With sufficiently high levels of electrical energy between the two electrodes, heat is generated which is sufficient to denature proteins within the tissue and cause cell death.

It is well known that by controlling the energy level, the amount of heat generated and degree of tissue damage can also be controlled. High levels of voltage can cut and remove tissue (i.e. electrosurgery), while lower levels will simply create sufficient heat to cause cell damage, but leave the structure intact and block electrical pathways within the tissue. Irrigation of the electrodes with saline or other conductive fluid can decrease the interface impedance, cool the tissue, and allow for a greater lesion depth. It is also know that a bipolar system (where the grounding electrode is in close proximity to the conductive tip) can create narrower and deeper lesions. At the limit, the grounding electrode is in the same dimension as the conductive tip, and both electrodes are used to create the lesion.

A bipolar ablation design may be created by integrating the electrode into the jaws of a hemostat (or forceps) like device. Mounting two electrodes onto the jaws of a forceps results in a tool that can clamp and ablate the tissue between the jaws.

A wide variety of surgical procedures involve ablation of selected tissue. One such procedure is the Maze procedure, which is a surgical operation for patients with atrial fibrillation that is resistant to medical treatment. In the conventional version of this procedure, incisions are created in the right and left atria to produce an orderly passage of the electrical impulse from the sino-atrial node (SA node) to the atrial-ventricular node (AV node). Blind passageways are also created to suppress reentry cycles. Ablation of cardiac conduction pathways in the region of tissue where electrical signals are malfunctioning is now being used to replace surgical incisions in the Maze procedure. Ablation is also used therapeutically with other organ tissues, such as the lungs, liver, prostate, and uterus. Ablation may also be used in treatment of disorders, such as tumors, cancers, or undesirable growths. There are various types of ablation devices that are in use and in development that are intended for use in the Maze procedure.

Sometimes ablation is necessary only at discrete positions along the tissue. At other times, ablation is desired along a line, called linear ablation. This is the case for atrial fibrillation, where the aim is to reduce the total mass of contiguous (electrically connected) atrial tissue below a threshold believed to be critical for sustaining multiple reentrant wavelets. Linear lesions are created between electrically non-conductive anatomic landmarks to reduce the contiguous atrial mass. One way of accomplishing linear ablation is to use a pair of bipolar electrosurgical forceps having jaws with an elongated electrode or series of electrodes used to apply energy to tissue for ablation purposes. One embodiment of this approach is described in U.S. patent Publication No. 2003/0171745, published Sep. 11, 2003, and titled "Ablation System and Method of Use," which is incorporated herein by reference in its entirety.

In conjunction with the use of electrosurgical ablation devices, various control mechanisms have been developed to control delivery of ablation energy to achieve the desired result of ablation (killing of cells at the ablation site while leaving the basic structure of the organ to be ablated intact). Additionally, there has been substantial work done toward assuring that the ablation procedure is complete, i.e. that the ablation extends through the thickness of the tissue to be ablated, before terminating application of ablation energy. This desired result is referred to as "transmural" ablation. Non-transmural lesions may be capable of propagating a depolarization wave form, or action potential and may not be effective in treating an arrhythmia. One embodiment of a system for assessing the transmurality of an ablation lesion is described in U.S. patent Publication No. 2003/0195384, published Oct. 16, 2003, and titled "System and Method for Assessing Transmurality of Ablation Lesions," which is incorporated herein by reference in its entirety.

One challenge associated with ablation procedures relates to determining the proper energy to apply to the tissue and duration of application of that energy in order to achieve the desired transmurality. One approach is to estimate tissue thickness and then to consult a look-up table to determine an experimentally determined energy and duration associated with that thickness. However, such an approach requires an accurate assessment of tissue thickness, which may also present a challenge. Further, depending on the type of device used to apply ablation energy to the tissue, further variables may be introduced. For example, when using a hemostat type device, the pressure between the jaws is a function of the force applied to the handles any may vary depending on the person holding the device. Such variability impacts the most effective treatment time and energy.

The design challenge with any ablation device, and in particular with a hemostat type device, is to create a lesion having consistent quality, in particular a continuous linear lesion when engaging in the Maze procedure. Further, it is desirable to create a lesion that is not too wide and that may be created in the least amount of time. Further, a challenge in the creation of such a device is to reduce the variability based upon the user such that a device may be used by various users with consistent results.

Accordingly, there is a need for an ablation device that is configured to permit a consistent application of appropriate force at the tissue site when in use. Further, there is a need for a device configured to permit real time assessment of lesion transmurality while in use. Further still, there is a need for an ablation device having the ability to aid in the determination of ablation parameters, such as degree of applied force, time of treatment, and treatment energy.

It would be desirable to provide a system and/or method that provides one or more of these or other advantageous features. Other features and advantages will be made apparent from the present specification. The teachings disclosed herein extend to those embodiments that fall within the scope of the appended claims, regardless of whether they accomplish one or more of the aforementioned needs.

SUMMARY OF THE INVENTION

The invention relates to a tissue ablation system having a handle and an ablation head coupled to the handle. The ablation head has a first jaw and a second jaw and an ablative element coupled to at least one of the first and second jaws. A thickness measurement device is coupled to the ablation head. The thickness measurement device indicates a distance separating the first and second jaws.

The invention further relates to a tissue ablation system having a handle and an ablation head coupled to the handle. The ablation head has a first jaw and a second jaw and an ablative element coupled to at least one of the first and second jaws. A force measurement device is coupled to the ablation head. The force measurement device indicates the force being applied by the first and second jaws on a piece of tissue disposed between the first and second jaws.

The invention further relates to a tissue ablation system having a handle and an ablation head coupled to the handle. The ablation head has a first jaw and a second jaw and an ablative element coupled to at least one of the first and second jaws. A strain measurement device is coupled to the ablation head. The strain measurement device indicates the strain resulting in a piece of tissue disposed between the first and second jaws when a stress is applied to the tissue.

The invention further relates to a method of assessing the transmurality of an ablation lesion in a piece of tissue during the performance of a surgical ablation procedure. The method includes the steps of applying a stress to the piece of tissue and calculating a strain in the tissue resulting from the application of the stress. The method further includes the step of determining the degree of transmurality of the ablation lesion based upon the strain and the stress.

The invention further relates to a method of ablating tissue. The method includes the steps of providing a bipolar ablation device having a pair of jaws, the jaws having one or more ablation electrodes, inserting the tissue between the jaws, and closing the jaws until the jaws engage the tissue. The method further includes the steps of measuring a thickness of the tissue by determining the distance between the jaws, selecting a jaw force, selecting an electrode energy, and selecting a time of energy application. The method further includes the steps of applying the selected jaw force to the tissue, energizing the one or more ablation electrodes to apply the selected electrode energy, and deenergizing the one or more ablation electrodes after the selected time has elapsed.

The invention is capable of other embodiments and of being practiced or carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION OF THE PREFERRED EMBODIMENTS

Figure 1:
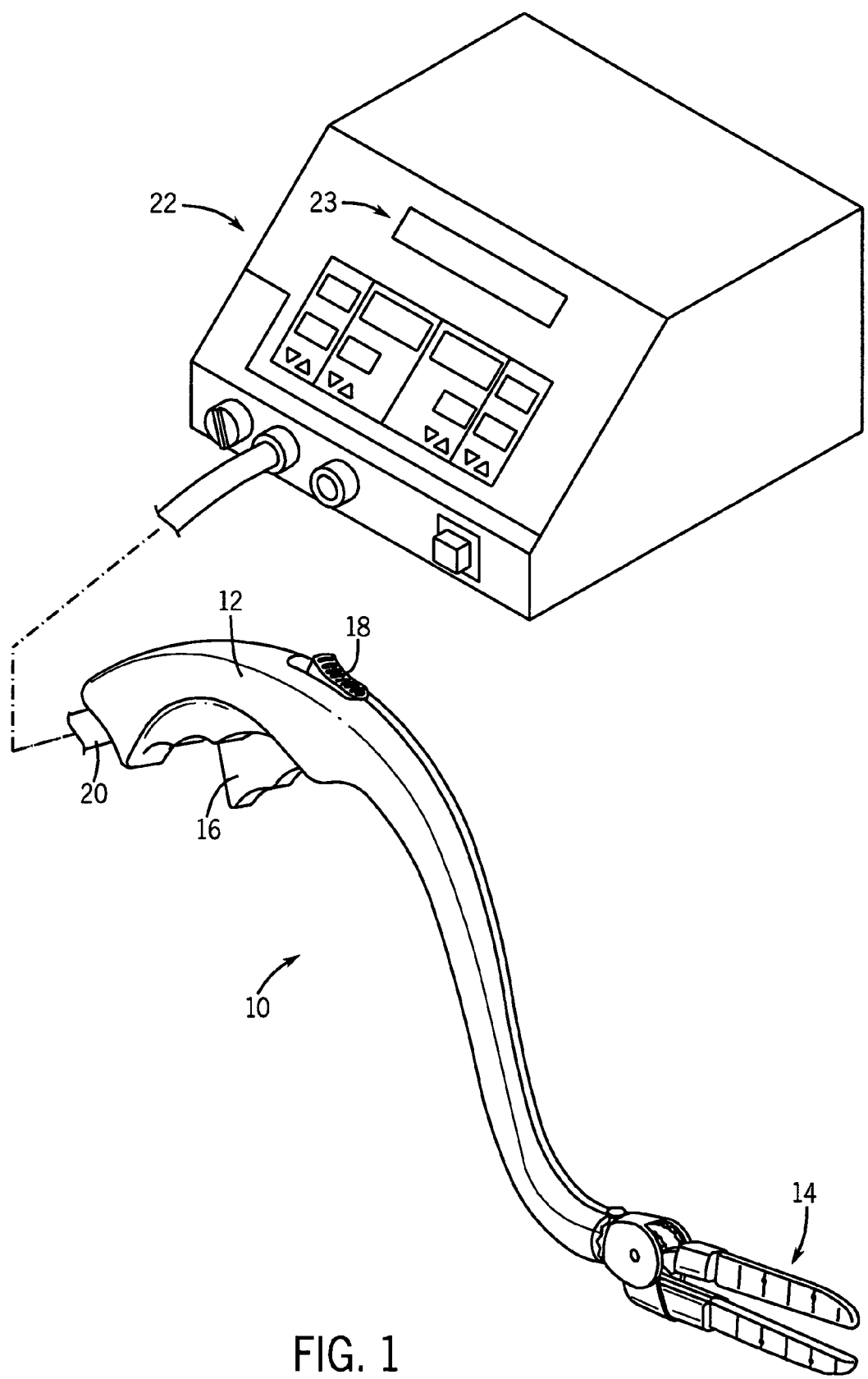
FIG. 1 is a schematic perspective view of a tissue ablation system.

Referring to FIG. 1, a tissue ablation device, shown as a bipolar ablation device 10 has a handle 12 and an ablation head 14. A trigger 16 may be used by a surgeon to control certain functions of the ablation head 14. A switch, shown as locking mechanism 18, may be utilized to lock the ablation head 14 into position during a surgical procedure.

Further referring to FIG. 1, in an exemplary embodiment of a tissue ablation system, bipolar ablation device 10 may be partially controlled by and may provide feedback to a control device, such as generator 22. A cord 20 serves as a conduit for various smaller cords and tubes between generator 22 and ablation device 10. For example, cord 20 may house a power line for ablation head 14, saline irrigation lines to and from ablation head 14, and various other wires and cords sending signals to and receiving signals from ablation head 14. An exemplary bipolar ablation device having many of the features described with respect to FIG. 1 is the CARDIOBLATE BP™ brand ablation system, available from Medtronic, Inc.

Figure 2:
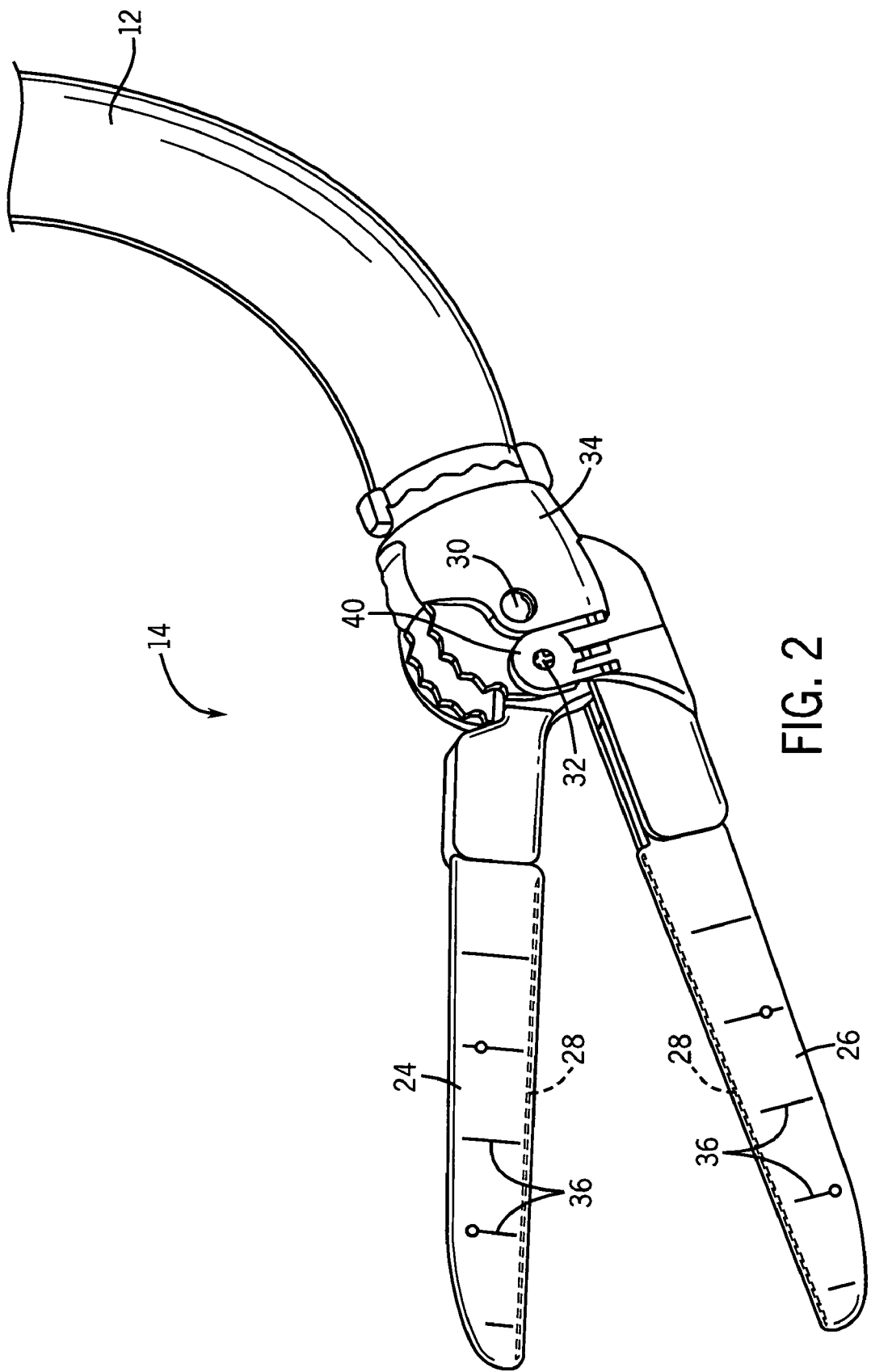
FIG. 2 is a perspective view of the head of a bipolar tissue ablation device having a thickness gauge.

Referring to FIG. 2, in an exemplary embodiment, ablation head 14 has a pair of jaws 24, 26. One or both of the jaws 24, 26 may have an ablative element for ablating tissue. The ablative element is typically an energy transfer device. In the embodiment shown in FIG. 2, ablative elements are shown as linear electrodes 28, that are used to impart RF energy to tissue for ablation purposes. There are many types of ablative elements and electrodes that may be used for ablation purposes, some of which are described in U.S. patent Publication No. 2003/0171745.

Further referring to FIG. 2, one jaw 24 may be pivotally coupled to the other jaw 26 via a pivot point 32 so that the jaws 24, 26 may be opened and closed via a mechanical or electromechanical mechanism known in the art. Further, jaw 26 is shown as being rotatably coupled to a base 34 via a pivot point 30, allowing jaws 24, 26 to be rotated together with respect to base 34. Base 34 is coupled to handle 12 and may have a mechanism allowing for quick removal from handle 12. In an exemplary embodiment, jaws 24, 26 are approximately seven centimeters in length and the electrodes 28 are each approximately five centimeters in length. Jaws 24, 26 may have length markings 36 to aid in their performance of surgical procedures. Further, jaws 24, 26 may be malleable such that a surgeon may curve the jaws to conform to a desired ablation lesion shape.

Further referring to FIG. 2, a thickness measurement device shown as thickness gauge 40 may be coupled to ablation head 14 in an exemplary embodiment. The thickness gauge 40 is used to determine the thickness of material placed between jaws 24, 26. One such way of determining the thickness of material between jaws 24, 26 is for thickness gauge 40 to be a potentiometer or rheostat coupled to the ablation head 14 at pivot point 32. Such a potentiometer may provide an electronic output signal representative of the distance between jaws 24, 26, the signal changing as upper jaw 24 is rotated with respect to lower jaw 26. In an exemplary embodiment, the signal provided by the potentiometer may be converted by the generator 22 (see FIG. 1) into a reading representative of the distance between jaws 24, 26, indicating the thickness of a piece of tissue between jaws 24, 26. The reading may be shown on a display 23 (see FIG. 1).

Although thickness gauge 40 is shown as a potentiometer or rheostat in FIG. 2, other thickness measurement devices may also be used, such as an ultrasonic thickness gauge or markings on the head 14 providing a visual indication of the distance between jaws 24, 26. Alternatively, receiver/transmitter pairs may be inserted into the jaws that electronically measure the distance between the electrodes and therefore the thickness of tissue between the jaws. In the embodiment depicted in FIG. 2, the jaws are pivotally coupled to one another so the distance between the jaws may be related to the angle between the jaws. However, in other systems where the jaws are adjusted in a linear fashion, thus maintaining the electrodes parallel with one another, the measured distance may be in units of length. Even when the measurement is made in degrees, the number of degrees may be converted to a reading in units of length, such as to provide the distance between the midpoints of each of the jaws 24, 26.

Figure 3:
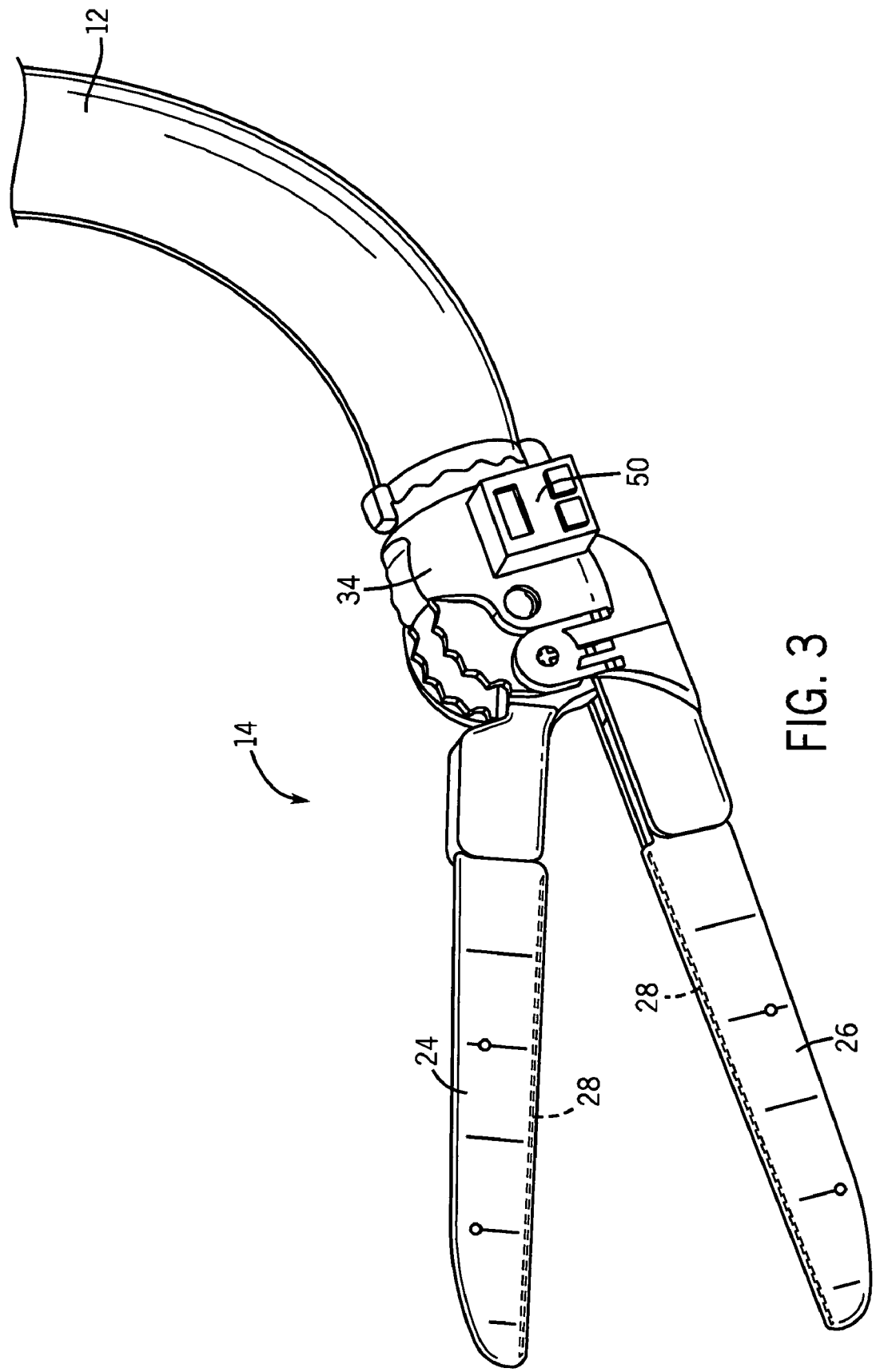
FIG. 3 is a perspective view of the head of a bipolar tissue ablation device having a force meter.

Referring to FIG. 3, in an exemplary embodiment, a force measurement device, shown as force meter 50 is incorporated into ablation head 14. The force meter 50 provides a measurement of the force being applied between jaws 24, 26 on material, such as tissue placed between jaws 24, 26. Various types of force meters used to provide an indication of the force between a pair of jaws are known in the mechanical arts.

The force meter 50 may provide a direct indication of the force being applied between the electrodes 28 or may alternatively provide an electronic signal representative of the force to another instrument, such as generator 22, which may then convert the electronic signal into a reading representative of the force being applied. In one embodiment, the jaws 24, 26 are closed by depressing trigger 16 (see FIG. 1). In such a case, a user may apply a certain amount of force to trigger 16 resulting in an appropriate force between jaws 24, 26 as indicated by force meter 50. The user may then lock the jaws 24, 26 into place with locking mechanism 18 prior to energizing linear electrodes 28. Alternatively, a user may program an appropriate jaw force into generator 22, for example, which may automatically close jaws 24, 26 over a desired piece of tissue and apply the desired amount of force, without the user having to depress trigger 16. While the force meter 50 is shown as being attached to base 34, it is to be understood that a force measurement device providing the desired functionality of force meter 50 may be placed in several different locations on bipolar ablation device, depending on the method by which the force between jaws 24, 26 is measured.

Figure 4:
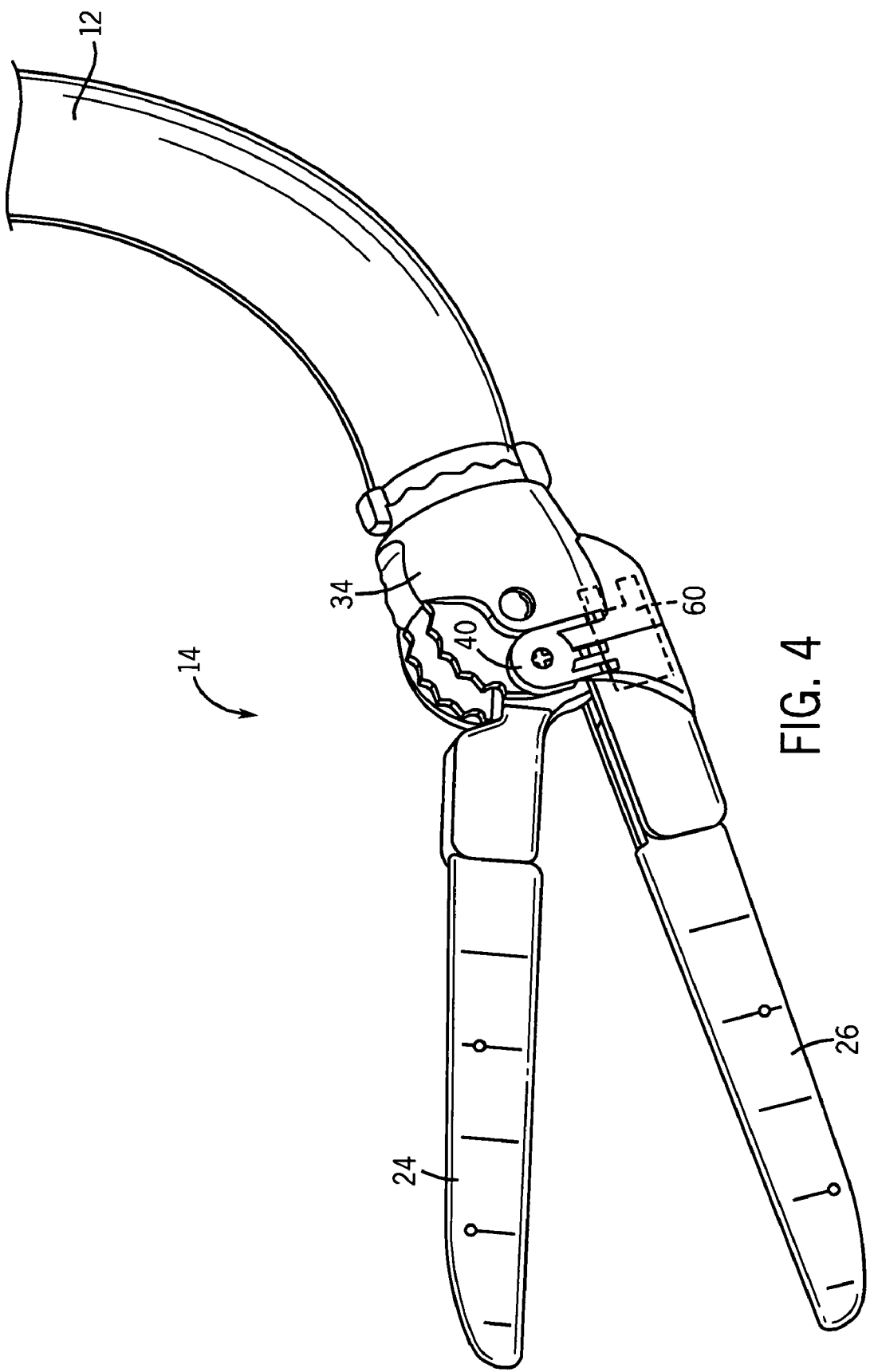
FIG. 4 is a perspective view of the head of a bipolar ablation device having a strain gauge integrated therein.

Referring to FIG. 4, in an exemplary embodiment, a strain measurement device, shown as strain gauge 60, may be incorporated into bipolar ablation device 10. The strain gauge 60 may be used to determine the amount of strain resulting in a material between jaws 24, 26 due to an applied stress. Various types of strain gauges are known in the art. The strain in the material between jaws 24, 26 may be calculated by any of a number of methods, such as by calculating the ratio of the distance of compaction of the material between jaws 24, 26 and the original thickness of the material between jaws 24, 26. The strain gauge 60 may automatically calculate the strain, or the strain may be calculated by an external instrument, such as generator 22, utilizing inputs provided by the strain gage 60 or other devices in the head 14, such as the thickness gauge 40. The output from strain gauge 60 may be utilized in other calculations as discussed below.

Figure 5:
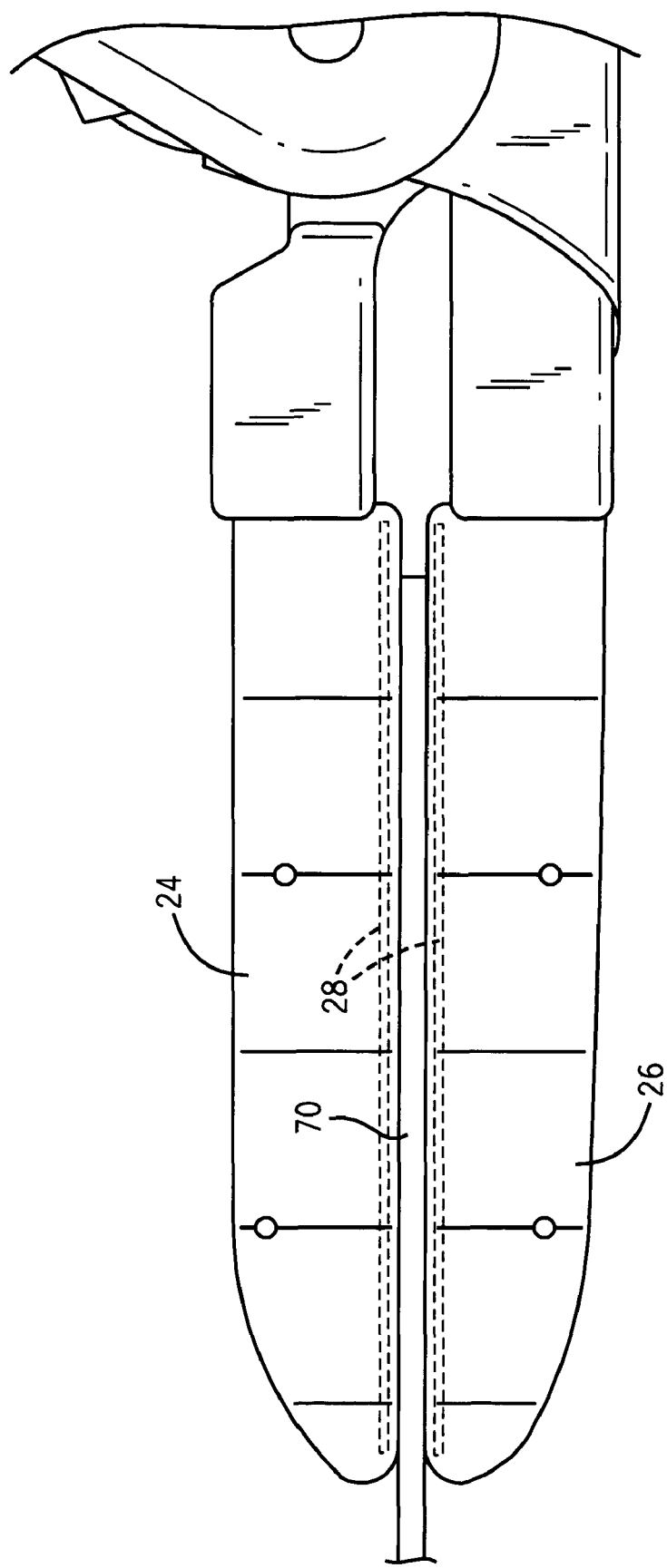
FIG. 5 is an elevation view of the head of a bipolar ablation device engaging a piece of tissue.

Referring to FIG. 5, in the performance of certain surgical procedures, such as a Maze procedure, the bipolar ablation device is used to create ablation lesions in tissue, such as heart tissue. In the performance of such a procedure utilizing bipolar ablation device, jaws 24, 26 are placed over a selected portion of tissue 70. An electrode energy is then selected along with a desired degree of force to be applied to tissue 70 between jaws 24, 26. Further, an ablation time may be selected that corresponds to the thickness of tissue 70 and the force being applied between jaws 24, 26.

In order to access the tissue to be ablated, a surgeon must first open an aperture into a patient's body. In the performance of a Maze procedure, access to the patient's heart may be provided via an open chest, such as utilizing a median sternotomy. Alternatively, access to the heart may be provided via a minimally invasive approach, such as with endoscopic tools on a "closed" chest, using one or more small incisions or ports. The Maze procedure may be performed on a beating heart, or on a stopped heart, requiring the use of a heart lung machine to place the patient on cardiopulmonary bypass. The locations of the lesions made in the performance of a Maze procedure, as well as methods of accessing the heart, are known in the art.

In order to create a lesion, the surgeon inserts a selected portion of tissue 70 between jaws 24, 26 and closes the jaws on the tissue 70 using an appropriate amount of force. The jaws may be closed utilizing the trigger 16 (see FIG. 1) or may be done automatically from signals sent from generator 22 or other control device.

Prior to selecting the ablation parameters such as RF energy, force, and time, the surgeon may wish to know the tissue thickness. The thickness gauge 40 may be utilized to provide the thickness parameter by closing the jaws 24, 26 over the selected portion of tissue 70 and providing a visual indication of or signal representative of the thickness of tissue 70.

After determining the thickness of tissue 70, the surgeon may apply an appropriate amount of force using jaws 24, 26 prior to engaging electrodes 28. In order to provide accuracy in the amount of force applied, the force meter 50 of the present invention may be utilized to measure the force being applied. The amount of force may be visually read by the surgeon or may be provided in an electronic signal representative of the force to a control unit such as generator 22.

After closing the jaws 24, 26 on tissue 70 at the appropriate degree of force, the surgeon may lock the jaws into place at that degree of force utilizing locking mechanism 18. Alternatively, robotic control of the jaws may be provided by a control device, such as generator 22, rather than a manual locking mechanism 18. At this point, the surgeon may engage linear electrodes 28 to begin the creation of an ablation lesion in tissue 70. During the application of RF energy to create the ablation lesion, saline may be applied to the ablation area between electrodes 28 to cool the tissue 70. Saline may be provided to jaws 24, 26 via a saline irrigation line connected to a saline source.

Once an RF energy and force of application have been selected and the tissue thickness has been determined, a surgeon may determine the time of energy application necessary to accomplish the goal of a transmural lesion. The time may be selected from experimental results for a particular type of tissue. Particularly when performing a Maze procedure, it is desirable to select the proper amount of time to ensure lesion transmurality, as a non-transmural ablation may not accomplish the goal of the procedure, and applying energy for too much time may damage the tissue more than necessary. Once the time of energy application has been determined, the surgeon may activate the electrodes 28 to ablate the tissue 70 between jaws 24, 26. After a transmural lesion has been created, the surgeon opens the jaws 24, 26 and repositions the bipolar ablation device to another region of tissue or removes the device from the patient's body and completes the procedure.

Although a precise tissue thickness measurement and application of force aids in accurately determining the amount of time necessary to create a transmural lesion, it may be beneficial to provide an indicator of lesion transmurality to ensure success of the procedure. Visual assessment of the tissue to determine transmurality may be inconvenient or impossible depending on the location of the tissue being ablated and the type of ablation device. Methods of assessing the transmurality of ablation lesions have been disclosed, such as the temperature assessment method disclosed in U.S. patent Publication No. 2003/0195384.

Figure 6:
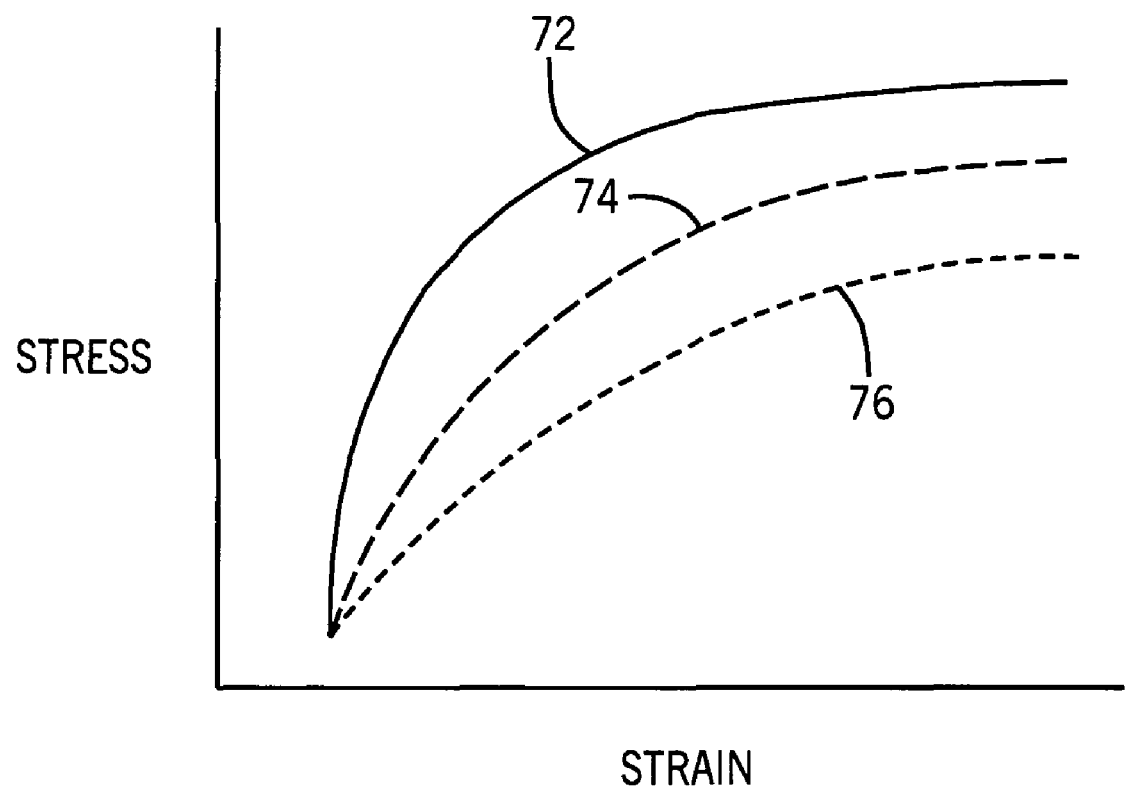
FIG. 6 is a chart showing exemplary stress versus strain curves for tissues in various states of ablation.

According to one embodiment of the invention, the bipolar ablation device 10 provides a method of assessing lesion transmurality. The method may be utilized while the electrodes are energized to provide a real time assessment of lesion transmurality or may be utilized after electrodes have been utilized to create a lesion, to ensure the proper depth of ablation. It is known that ablated tissue exhibits a different strain for a given amount of stress than does non-ablated tissue. Referring to FIG. 6, hypothetical stress versus strain curves are shown to indicate the difference in strain for a given application of stress for ablated and non-ablated tissues. For example, curve 72 may correspond to fully ablated tissue in which complete transmurality has been achieved, curve 74 may correspond to partially ablated tissue, and curve 76 may correspond to non-ablated tissue.

As described above, certain embodiments of the present invention are described as having a strain measurement device, such as strain gauge 60, and a force measurement device such as force meter 50. These elements may be combined to provide the information necessary to utilize stress versus strain data to determine lesion transmurality. A given amount of stress may be applied to the tissue utilizing force meter 50 as an indicator of the force being applied over the area of the jaws. Alternatively, the selected amount of stress may be applied automatically using a control device such as generator 22. The resultant strain may be directly measured using strain gauge 60, but may also be calculated using thickness gauge 40 to calculate the change in thickness resultant from the applied stress versus the original thickness of the tissue.

The strain measurement may be quickly performed during a procedure while the electrodes are activated if desired. If this is the case, a control device, such as generator 22, may be programmed to perform real time assessments of lesion transmurality and automatically cease the application of RF energy through electrodes 28 when lesion transmurality has been accomplished. Further, stress versus strain curves for a number of degrees of lesion transmurality may be generated and programmed into generator 22 such that the user may be provided a real time indication of depth of ablation as a procedure is being performed.

While the concepts of measuring tissue thickness, force application, and tissue strain are described with respect to a bipolar ablation device, such concepts may be useful when applied to other types of ablation devices such as an electrocautery device, an electrosurgical device, an ablation paddle, and an ablation wire, among other types of devices. A set up similar to that shown in FIGS. 1-5 may be utilized, for example by replacing the ablation head 14 with a different type of ablation device. Further, ablation may be accomplished using ultrasonic energy, microwave energy, or a cryogenic approach, instead of or in addition to the RF energy described herein.

The bipolar ablation device and system may be used in procedures requiring tissue ablation in the heart as described herein. However, the ablation device and system may also be used on other tissues (e.g. lungs, liver, prostate, etc.) and in other types of surgical procedures that require tissue ablation.

The generator depicted in FIG. 1 may be used to provide power to bipolar ablation device 10 and to control the various parts that are subject to automatic control, such as the opening, closing, and positioning of ablation head 14 and jaws 24, 26. The generator may have various visual displays, such as the force being applied, the thickness of a selected piece of tissue, and the degree of lesion transmurality (such as percentage complete). The generator may also incorporate other functions associated with surgical procedures, such as functioning as a cardiac monitor.

While the detailed drawings and specific examples given herein describe various exemplary embodiments, they serve the purpose of illustration only. It is to be understood that the invention is not limited in its application to the details of construction and the arrangements of components set forth in the preceding description or illustrated in the drawings. For example, in various embodiments described in this application, a force measurement device, a thickness measurement device, and a strain measurement device are described. These may be used separately on devices, or in various combinations as desired. Furthermore, other substitutions, modifications, changes, and omissions may be made in the design, operating conditions, and arrangements of the exemplary embodiments without departing from the scope of the invention as expressed in the appended claims.

What is claimed is:

1. A tissue ablation system comprising:
   a handle;
   an ablation head coupled to the handle, the ablation head having a first jaw and a second jaw adapted to apply a force on tissue disposed between the first and second jaws;
   an ablative element coupled to at least one of the first and second jaws for delivering an ablative energy to tissue disposed between the first and second jaws;
   a thickness measurement device coupled to the ablation head, wherein the thickness measurement device outputs an electrical signal that indicates a distance separating the first and second jaws; and
   a generator electrically coupled to the ablation head, wherein the generator controllably delivers RF ablative energy to the ablative element to form a transmural ablation lesion in tissue disposed between the first and second jaws for an ablation time period that is determined based on at least the electrical signal outputted from the thickness measurement device and that is electrically provided to the generator; and
   the generator having a display and wherein the distance separating the first and second jaws is shown on the display.

2. The tissue ablation system of claim 1, wherein the thickness measurement device is a thickness gauge.

3. The tissue ablation system of claim 2, wherein the thickness gauge is a potentiometer.

* * * * *